United States Patent [19]

Kjellin

[11] Patent Number: 4,777,255

[45] Date of Patent: Oct. 11, 1988

[54] PROCESS FOR PREPARING A PURINE DERIVATIVE

[75] Inventor: Per G. Kjellin, Lund, Sweden

[73] Assignee: Aktiebolaget Draco, Sweden

[21] Appl. No.: 62,952

[22] Filed: Jun. 16, 1987

[30] Foreign Application Priority Data

Jun. 27, 1986 [SE] Sweden .................................. 8602887

[51] Int. Cl.$^4$ ..................... C07D 473/06; A61K 31/52
[52] U.S. Cl. ..................................... 544/273; 544/267
[58] Field of Search ................. 544/273, 267; 514/262, 514/263

[56] References Cited

U.S. PATENT DOCUMENTS 2,852,516 9/1958 Comte .............................. 260/256.4
4,325,956 4/1982 Kjellin .................................. 514/263

FOREIGN PATENT DOCUMENTS

ES537595 11/1984 Spain .

OTHER PUBLICATIONS

Chemical Abstracts, vol. 85, Abstract No. 177 473n (1976).

Primary Examiner—Nicholas S. Rizzo
Attorney, Agent, or Firm—Brumbaugh, Graves, Donohue & Raymond

[57] ABSTRACT

A method for the preparation of enprofylline is disclosed, which method comprises (a) treating 6-amino-1-n-propyl-2,4-(1H,3H)-pyrimidinedione in formic acid with sodium nitrite in the presence of a catalyst to the formation of 6-amino-5-formamido-1-n-propyl-2,4-(1H,3H)-pyrimidinedione and (b) performing a ring-closure reaction on the formed 6-amino-5-formamido-1-n-propyl-2,4-(1H,3H)-pyrimidinedione to the formation of 3,7-dihydro-3-n-propyl-1H-purin-2,6-dione.

3 Claims, No Drawings

PROCESS FOR PREPARING A PURINE DERIVATIVE

FIELD OF THE INVENTION

The present invention relates to a novel method for the preparation of 3,7-dihydro-3-n-propyl-1H-purine-2,6-dione (enprofylline), which has the formula

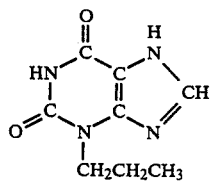
(I)

PRIOR ART

Enprofylline and methods for its preparation are disclosed in i.a. U.S. Pat. No. 4,325,956.

One of these methods comprises the following reaction steps

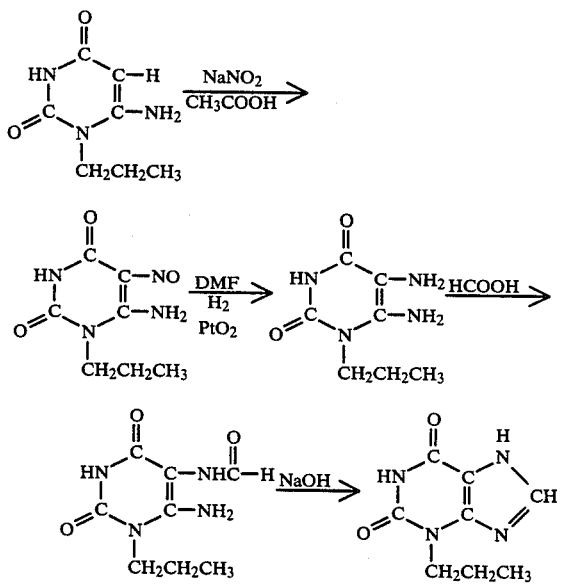

This method has several drawbacks:

1. It requires large volumes of solvents, which makes its use in big scale processes impossible,
2. The intermediates must be isolated, which makes the production more expensive, and
3. The process is run in several vessels, which prolongs the time of synthesis.

Accordingly an object of the present invention is to provide a novel method for the preparation of enprofylline, which method is easier, faster and cheaper than the above mentioned prior art method.

DISCLOSURE OF THE INVENTION

It has now surprisingly been found that enprofylline can be prepared from an uracil in a two step process in which the first step comprises the conversion of the uracil to a amide in one single vessel with the intermediation of formic acid and the second step is a ring closure reaction of the amide to the formation of enprofylline:

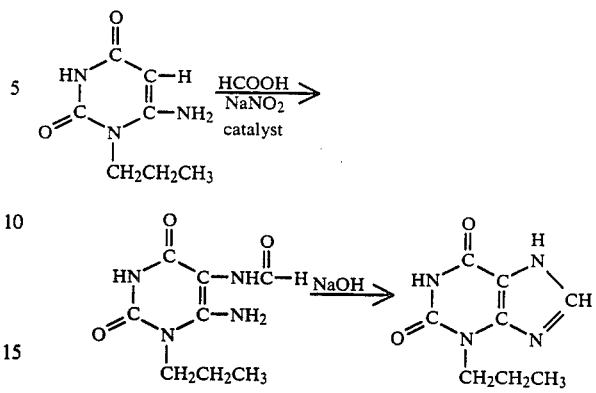

Accordingly, the present invention provides a method for the preparation of 3,7-dihydro-3-n-propyl-1H-purine-2,6-dione (enprofylline), which method is characterized in (a) treating 6-amino-1-n-propyl-2,4-(1H,3H)-pyrimidinedione in formic acid with sodium nitrite in the presence of a catalyst to the formation of 6-amino-5-formamido-1-n-propyl-2,4-(1H,3H)-pyrimidinedione and (b) performing a ring-closure reaction on the formed 6-amino-5-formamido-1-n-propyl-2,4-(1H,3H)-pyrimidinedione to the formation of 3,7-dihydro-3-n-propyl-1H-purin-2,6-dione.

The use of formic acid in the method of the invention is particularly crucial. The formic acid acts with the following purposes:

1. As a solvent. It is a good solvent for all substances included in the reaction. These substances are very difficult to disolve in most other solvents.
2. As an acid for the generation of $HNO_2$ from $NaNO_2$ at the forming of the NO-moiety.
3. As a reduction agent through its decomposition by a catalyst into $H_2$ and $CO_2$ in the presence of the nitroso compound. The hydrogen gas is used for the reduction of the nitroso compound to the diamine.
4. As a reagent by forming formamide from the diamine.

The catalyst used in step (a) is Pt/C, $PtO_2$, Pd/C or Rh/C, preferably Pt/C.

The reaction in step (a) is usually preformed at a gentle heating 30°–100°, preferably 30°–50° C.

The compound of step (a), 6-amino-5-formamido-1-n-propyl-2,4-(1H,3H)-pyrimidinidione, may be isolated before it is used in step (b) but it could also be used directly without previous isolation.

The ring closure reaction of step (b) is performed in a conventional manner, such as for instance by addition of a sodium hydroxid solution (i.a. 45 %) to 6-amino-5-formamide-1-n-propyl-2,4-(1H,3H)-pyrimidine-dione and gently heating (80°–100° C.) the mixture, or by heating to the melting point or by heating in a solvent such as polyphosphorous acid or sulfolane. The precipition of formed enprofylline is carried out by the additon of hydrochlorid acid and the further working up is performed in a conventional way.

BEST MODE FOR CARRING OUT THE INVENTION

The invention will in the following be illustrated by means of a number of working examples without being limited thereto.

EXAMPLE 1 Preparation of 6-amino-5-formamido-1-propyl-2,4-(1H,3H)-pyrimidinedione (a) Sodium nitrite (21.0 g) was dissolved in 20 ml water and added to a suspension of 6-amino-1-propyl-2,4-(1H,3H)-pyrimidinedione (50 g) in formic acid (150 ml). $PtO_2$ (0.2 g) was added and the reaction mixture was heated to 80° C. Evolution of carbon dioxide was observed. The catalyst was filtered off. The product was precipitated by cooling and filtered off, washed with water and ethanol. Yield 53.5 g (85 %).

(b) Preparation of the title compound was performed according to the description of Example 1a but the catalyst $PtO_2$ was exchanged to Pd/C or Rh/C.

(c) Sodium nitrite (127 kg) was dissolved in water and added to suspension of 6-amino-1-propyl-2,4-(1H,3H)-pyrimidinedione (300 kg) in formic acid (1 400 kg). Pt/C 5 % was added and the reaction mixture heated to 40°–80° C. The catalyst was filtered off, formic acid was distilled off and ethanol (870 kg) was added. The product was precipitated by cooling and isolated by centrifugation, washed with ethanol/water and used directly in Example 2.

EXAMPLE 2 Preparation of 3,7-Dihydro-3-propyl-1H-purine-2,6-dione (Enprofylline)

6-Amino-5-formamido-1-propyl-2,4-(1H,3H)-pyrimidinedione (450 kg) was added to a solution of sodium hydroxide liquid 45 % (130 kg) and water. The mixture was heated and the product was precipitated by addition of hydrochloric acid. The reaction mixture was cooled and the product was isolated by centrifugation, washed with ethanol/water. This was dissolved in sodium hydroxide liquid 45 % (130 kg) and water. After treatment with activated carbon (10 kg) the product was precipitated by addition of hydrochloric acid to pH 5–6, centrifugated, washed with water and dried in vacuo to constant weight. Yield about 248 kg. The obtained product was identified by NMR as the title compound.

I claim:

1. Method for the preparation of 3,7-dihydro-3-n-propyl-1H-purine-2,6-dione, characterized in
   (a) treating 6-amino-1-n-propyl-2,4-(1H,3H)-pyrimidinedione in formic acid with sodium nitrite in the pressence of a catalyst selected from the group consisting of Pt/C, $PtO_2$, Pd/C and Rh/C to the formation of 6-amino-5-formamido-1-n-propyl-2,4-(1H,3H)-pyrimidinedione and
   (b) performing a ring closure reaction on the formed 6-amino-5-formamido-1-n-propyl-2,4-(1H,3H)-pyrimidinedione to the formation of 3,7-dihydro-3-n-propyl-1H-purine-2,6-dione.

2. Method according to claim 1, characterized in that 6-amino-1-n-propyl-2,4-(1H,3H)-pyrimidinedione is converted to 6-amino-5-formamido-1-n-propyl-2,4-(1H,3H)-pyrimidinedione by the intermediation of formic acid.

3. Method according to claim 1, characterized in using as catalyst in step (a) Pt/C.

* * * * *